United States Patent
De Haan et al.

(10) Patent No.: US 12,064,269 B2
(45) Date of Patent: *Aug. 20, 2024

(54) DEVICE, SYSTEM AND METHOD FOR GENERATING A PHOTOPLETHYSMOGRAPHIC IMAGE CARRYING VITAL SIGN INFORMATION OF A SUBJECT

(71) Applicant: KONINKLIJKE PHILIPS N.V., Eindhoven (NL)

(72) Inventors: Gerard De Haan, Helmond (NL); Moco Andreia, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 186 days.

This patent is subject to a terminal disclaimer.

(21) Appl. No.: 17/520,753

(22) Filed: Nov. 8, 2021

(65) Prior Publication Data

US 2022/0054089 A1 Feb. 24, 2022

Related U.S. Application Data

(63) Continuation of application No. 16/069,191, filed as application No. PCT/EP2017/050622 on Jan. 13, 2017, now Pat. No. 11,191,489.

(30) Foreign Application Priority Data

Jan. 15, 2016 (EP) ..................................... 16151494

(51) Int. Cl.
*A61B 5/00* (2006.01)
*A61B 5/024* (2006.01)
(Continued)

(52) U.S. Cl.
CPC .......... *A61B 5/7214* (2013.01); *A61B 5/0036* (2018.08); *A61B 5/02433* (2013.01);
(Continued)

(58) Field of Classification Search
CPC . A61B 5/7214; A61B 5/0036; A61B 5/02433; A61B 5/1102; A61B 5/1128;
(Continued)

(56) References Cited

U.S. PATENT DOCUMENTS 10,521,900 B2  12/2019  Bartula et al.
2011/0251493 A1  10/2011  Poh
(Continued)

OTHER PUBLICATIONS

Markus Hulsbusch, Ein bildgestutztes, funktionelles Verfahren zur optoelektronischen Erfassung der Hautperfusion, Dissertation Technischen Hochschule Aachen,, Jan. 28, 2008, USPTO provided translation on 4.2, 4.3, 4.4.3, 6.2.1, 6.5.*

(Continued)

*Primary Examiner* — Bo Joseph Peng

(57) ABSTRACT

The present invention relates to a device, system and a method for generating a photoplethysmographic image carrying vital sign information of a subject. To provide an increased validity and robustness against motion, in particular against ballistocardiographic motion, the proposed device comprises an input interface (30) for obtaining image data of a skin region of a subject in at least two different wavelength channels, said image data comprising two or more image frames acquired by detecting light transmitted through or reflected from the skin region over time, wherein said image data comprise wavelength-dependent reflection or transmission information in said at least two different wavelength channels, a combination unit (31) for combining, per pixel or group of pixels and per time instant, image data values of said at least two different wavelength channels to obtain a time-variant pulse signal per pixel or group of (Continued)

pixels, and an image generation unit (32) for generating a photoplethysmographic image from a property of the respective pulse signals in a time window including at least two image frames.

9 Claims, 3 Drawing Sheets

(51) Int. Cl.
*A61B 5/11* (2006.01)
*A61B 5/1455* (2006.01)
*H04N 23/11* (2023.01)
*G06T 7/00* (2017.01)

(52) U.S. Cl.
CPC .......... *A61B 5/1102* (2013.01); *A61B 5/1128* (2013.01); *A61B 5/14552* (2013.01); *A61B 5/7207* (2013.01); *H04N 23/11* (2023.01); *A61B 5/02427* (2013.01); *A61B 2576/00* (2013.01); *G06T 7/0012* (2013.01); *G06T 2207/10048* (2013.01); *G06T 2207/30076* (2013.01)

(58) Field of Classification Search
CPC .............. A61B 5/14552; A61B 5/7207; A61B 5/02427; A61B 2576/00; H04N 23/11; G06T 7/0012; G06T 2207/10048; G06T 2207/30076
See application file for complete search history.

(56) References Cited

U.S. PATENT DOCUMENTS

| | | | | |
|---|---|---|---|---|
| 2012/0105823 | A1* | 5/2012 | Hardegger | H04N 25/705 356/6 |
| 2012/0141000 | A1 | 6/2012 | Jeanne | |
| 2012/0195473 | A1* | 8/2012 | De Haan | G06T 7/20 382/107 |
| 2013/0271591 | A1* | 10/2013 | Van Leest | A61B 5/7207 348/77 |
| 2013/0294505 | A1* | 11/2013 | Kirenko | H04N 19/186 375/240.02 |
| 2014/0086462 | A1* | 3/2014 | Shan | G01N 21/25 382/128 |
| 2014/0192177 | A1* | 7/2014 | Bartula | A61B 5/14551 348/77 |
| 2014/0200460 | A1 | 7/2014 | Johnson | |
| 2014/0206965 | A1* | 7/2014 | De Haan | G06T 5/002 600/323 |
| 2014/0276089 | A1* | 9/2014 | Kirenko | G16H 40/67 600/407 |
| 2015/0051521 | A1 | 2/2015 | Woerlee et al. | |
| 2015/0164592 | A1 | 6/2015 | Elhawary | |
| 2015/0320363 | A1 | 11/2015 | De Haan | |
| 2015/0379370 | A1 | 12/2015 | Clifton | |

OTHER PUBLICATIONS

Wieringa et al., Wieringa, F.P., Mastik, F. & Steen, A.F.W.v.d. Contactless Multiple Wavelength Photoplethysmographic Imaging: A First Step Toward "SpO2 Camera" Technology. Ann Biomed Eng 33, 1034-1041, 2005, https://doi.org/10.1007/s10439-005-5763-2.*
RGB sources, RP Photonics Encyclopedia, Encyclopedia of Laser Physics and Technology, Wayback machine on Jul. 25, 2013, https://web.archive.org/web/20130725022106/http://www.rp-photonics.com:80/rgb_sources.html.*
M. Huelsbusch, "An image-based functional method for opto-electronic detection of skin-perfusion," Phd thesis, RWTH Aachen dept. of EE. (in German) (2008), Translated English abstract included.
Moco, et al., "Ballistocardiographic artifacts in PPG imaging", IEEE Transactions on Biomedical Engineering., Nov. 20, 2015.
Verkruysse et al., "Remote plethysmographic imaging using ambient light", Optics Express, 16(26), Dec. 22, 2008, pp. 21434-21445.
G. de Haan and A. van Leest, "Improved motion robustness of remote-PPG by using the blood volume pulse signature", Physiol. Meas. 35 1913, 2014.
Kamshilin, et al., "A new look at the essence of the imaging photoplethysmography," Sci. Rep. 5 (2015).
de Haan, et al., "Robust pulse-rate from chrominance-based rPPG", IEEE Transactions On Biomedical Engineering, vol. 60, No. 10, Oct. 2013.
Kamshilin, et al., "Photoplethysmographic imaging of high spatial resolution", Apr. 1, 2011 / vol. 2, No. 4 / Biomedical Optics Express.
Yan, et al., "Noncontact measurement of heart rate using facial video illuminated under natural light and signal weighted analysis", Bio-Medical Materials and Engineering 26 (2015) S903-S909.

* cited by examiner

DEVICE, SYSTEM AND METHOD FOR GENERATING A PHOTOPLETHYSMOGRAPHIC IMAGE CARRYING VITAL SIGN INFORMATION OF A SUBJECT

CROSS-REFERENCE TO PRIOR APPLICATIONS

This application is a continuation of U.S. patent application Ser. No. 16/069,191 filed Jul. 11, 2018 which is the U.S. National Phase application under 35 U.S.C. § 371 of International Application No. PCT/EP2017/050622, filed on Jan. 13, 2017, which claims the benefit of EP Patent Application No. EP 16151494.8 filed on Jan. 15, 2016. These applications are hereby incorporated by reference herein.

FIELD OF THE INVENTION

The present invention relates to a device, system and method for generating a photoplethysmographic image carrying vital sign information of a subject, such as a person (e.g. a patient, elderly person, baby, etc.) or animal.

BACKGROUND OF THE INVENTION

Vital signs of a person, for example the heart rate (HR), the respiration rate (RR) or the arterial blood oxygen saturation, serve as indicators of the current state of a person and as powerful predictors of serious medical events. For this reason, vital signs are extensively monitored in in-patient and out-patient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Conventional pulse oximeters (also called contact PPG device herein) for measuring the heart rate and the (arterial) blood oxygen saturation (also called SpO2) of a subject are attached to the skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmittance of the same area or volume of tissue at two different wavelengths. This is referred to as time-division-multiplexing. The transmittance over time at each wavelength gives the PPG waveforms for red and infrared wavelengths. Although contact PPG is regarded as a basically non-invasive technique, contact PPG measurement is often experienced as being unpleasant and obtrusive, since the pulse oximeter is directly attached to the subject and any cables limit the freedom to move and might hinder a workflow. The same holds for contact sensors for respiration measurements. Such contact sensors may sometimes be practically impossible because of extremely sensitive skin (e.g. of patients with burns and preterm infants).

Recently, non-contact, remote PPG (rPPG) devices (also called camera rPPG device herein) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Using PPG technology, vital signs can be measured, which are revealed by minute light absorption changes in the skin caused by the pulsating blood volume, i.e. by periodic color changes of the human skin induced by the blood volume pulse. As this signal is very small and hidden in much larger variations due to illumination changes and motion, there is a general interest in improving the fundamentally low signal-to-noise ratio (SNR). There still are demanding situations, with severe motion, challenging environmental illumination conditions, or high required accuracy of the application, where an improved robustness and accuracy of the vital sign measurement devices and methods is required, particularly for the more critical healthcare applications.

To achieve motion robustness, pulse-extraction methods profit from the color variations having an orientation in the normalized RGB color space which differs from the orientation of the most common distortions usually induced by motion. A known method for robust pulse signal extraction uses the known fixed orientation of the blood volume pulse in the normalized RGB color space to eliminate the distortion signals. Further background is disclosed in G. de Haan and A. van Leest, "Improved motion robustness of remote-PPG by using the blood volume pulse signature", Physiol. Meas. 351913, 2014, which describes that the different absorption spectra of arterial blood and bloodless skin cause the variations to occur along a very specific vector in a normalized RGB-space. The exact vector can be determined for a given light-spectrum and transfer-characteristics of the optical filters in the camera. It is shown that this "signature" can be used to design an rPPG algorithm with a much better motion robustness than the recent methods based on blind source separation, and even better than chrominance-based methods published earlier.

A next challenge in camera-based vital sign monitoring is PPG imaging. Essentially, the camera-based approach is used to map the spatially varying PPG amplitude and its derived vital signs (local SpO2, local perfusion, etc.). The hope is that this new technique will enable new diagnostic means, e.g. for wound-healing, analysis of lesions (on-skin or internally after or during surgery), and cancer-detection (e.g. melanoma, but maybe also oesophagus-cancer, colon-cancer, etc.).

A. A. Kamshilin, E. Nippolainen, I. S. Sidorov, P. V. Vasilev, N. P. Erofeev, N. P. Podolian, and R. V. Romashko, "A new look at the essence of the imaging photoplethysmography," Sci. Rep. 5 (2015) discloses a system that builds PPG images from a monochrome camera (and mentions operating this system at 525 nm, which is close to 550 nm where the PPG-amplitude is strongest).

Markus Hülsbusch: "Ein bildgestütztes, funktionelles Verfahren zur optoelektronischen Erfassung der Hautperfusion", Dissertation, Technische Hochschule Aachen, 28 Jan. 2008, discloses an optoelectronic camera based measurement concept for assessment of skin perfusion. For the detection and minimization of motion induced artifacts different strategies for movement compensation have been investigated.

SUMMARY OF THE INVENTION

It is an object of the present invention to provide a device, system and a method for generating a PPG image carrying vital sign information of a subject, which provide an increased validity and robustness against motion, in particular against ballistocardiographic (BCG) motion.

In a first aspect of the present invention, a device for generating a PPG image carrying vital sign information of a subject is presented, the device comprising:
- an input interface for obtaining image data of a skin region of a subject in at least two different wavelength channels, said image data comprising two or more image frames acquired by detecting light transmitted through or reflected from the skin region over time, wherein said image data comprise wavelength-dependent reflection or transmission information in said at least two different wavelength channels,
- a combination unit for combining, per pixel or group of pixels and per time instant, image data values of said at least two different wavelength channels to obtain a time-variant pulse signal per pixel or group of pixels, wherein said combination unit is configured to combine the image data values of said at least two different wavelength channels as a weighted combination of temporally normalized wavelength channels or of the logarithm of wavelength channels, wherein the sum of the weights used for the combination is substantially zero, and
- an image generation unit for generating a photoplethysmographic image from a property of the respective pulse signals in a time window including at least two image frames.

In a further aspect of the present invention, a system for generating a PPG image carrying vital sign information of a subject is presented, the system comprising:
- an imaging unit for acquiring image data of a skin region of a subject in at least two different wavelength channels, said image data comprising two or more image frames acquired by detecting light transmitted through or reflected from the skin region over time, wherein said image data comprise wavelength-dependent reflection or transmission information in said at least two different wavelength channels, and
- a device as disclosed herein for generating a photoplethysmographic image carrying vital sign information of a subject from the acquired image data.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

Using a monochrome camera signal, as done in a known method, absorption variations in the skin due to varying blood volume cannot be distinguished from variations due to motion. It is has been found that even if care is taken to limit the influence of motion, the means (narrow band-pass filtering around heart rate, correlating with a reference PPG signal) are ineffective, should the motion be synchronous to the pulse. Such cardiac-cycle synchronous motions are common near bigger arteries, and even palpable, and can be suspected to play a role at other places since the PPG-signal is very small. Particularly when the skin is non-uniformly illuminated, the angle between skin-normal and incident light is largest and the problem is exacerbated. The wrist's skin at the vicinity of the brachial artery provides a clear example.

In an experiment the skin covering the brachial artery was covered by opaque ink, so only artifacts are acquired by the ink sensors. It can be observed that the magnitude of ballistocardiographic motion artifacts is comparable to the strongest PPG signals at the palm (0.005 AC/DC), and exceeds the amplitude of neighboring PPG signals at the wrist by a factor of five.

The present invention proposes an approach to significantly reduce the influence of motion on the PPG image. In particular, a mapping of two or more different wavelength channels made such that the resulting pixel values are insensitive to motion, while still sensitive to PPG variations. Biophysical (i.e. vital sign related) information, such as a local PPG amplitude image or derived information is obtained by combining the image data of different wavelength channels acquired over a time window of at least two image periods (i.e. covering at least two image periods) into at least one output PPG image, which carries the biophysical information.

Hereby, the PPG image is generally generated from a property of the respective pulse signals in a time window including at least two image frames. In particular, variations of the pulse signal are evaluated and reflected as image values of the PPG image in a spatial location corresponding to the pulse signal. The output image is thus, per time window, a single PPG image showing, in preferred embodiments, as property of the pulse signal, a function of the local perfusion (or local pulsatility, which may be understood to be the amplitude of the AC signal part of the pulse signal (or PPG signal) normalized to the DC level of the pulse signal (or PPG signal)), or the local phase of the pulse signal (the phase changes, e.g. due to travelling times of the blood, which may also depend on the size of the blood vessels imaged locally), or the local amplitude of the pulse signal, or the standard deviation of the pulse signal. The output image thus captures the spatial variation of the respective property of the individual pulse signals. The scaling and bias (contrast and zero-level) of the spatial variation can be varied if required (e.g. automatic scaling for maximum contrast, or fixed scaling to know absolute pulsatility). The property may be mapped directly into an image, but may also be mapped using a linear or non-linear function, such as a gamma correction, subtraction of bias for improved contrast, squaring to show energy instead of amplitude, using the energy instead of amplitude, or variance instead of standard deviation, etc.

The image data values of said at least two different wavelength channels are combined as a weighted combination of temporally normalized wavelength channels or of the logarithm of wavelength channels, wherein the sum of the weights used for the combination is substantially zero. The present invention thus profits from the knowledge that motion, in particular BCG motion, causes different relative strengths in the wavelength channels than the PPG signal. Hülsbusch, instead, makes channel combinations (green and red) aiming at eliminating HF-ambient light flickering and applies a weighted combination minimizing the energy of the flickering. This cannot be used for eliminating BCG motion as this motion is pulse-frequent (same as the PPG-signal), and thus also no proper weight can be determined according to Hülsbusch. In contrast, according to the present invention time-normalized wavelength channels (or the logarithmic version of the wavelength channels) are used so that the BCG motion disappears by choosing weights that add up to zero.

The computations may also be repeated on (non-overlapping or partially overlapping) time windows and thus provide a video (i.e. an image sequence) of the time-evolution of e.g. the local perfusion.

In an embodiment said combination unit is configured to combine the image data values of said at least two different wavelength channels as a weighted average, in particular of temporally normalized wavelength channels, such that the sum of the weights is substantially zero and wherein said image generation unit is configured to compute an amplitude map and/or phase map of the temporal variations of said time-variant pulse signals as photoplethysmographic image.

In an embodiment said image generation unit is configured to compute the amplitude map as inner product of the respective pulse signal with a reference signal and/or for computing the phase of the phase map with respect to a reference signal. The device may further comprise a computation unit for computing said reference signal using a motion-robust photoplethysmography signal extraction algorithm. Hereby, the reference signal may be computed from a skin area covered by a plurality of pixels in said image frames (i.e. from a large skin area) using a normalized blood volume pulse vector signature based method (i.e. a Pbv method), a chrominance based method (i.e. a CHROM method), a blind source separation method (i.e. a BSS method), a principal component analysis (PCA) or an independent component analysis (ICA). The reference signal may thus be obtained from a signal obtained by averaging the signals of a selected group of pixels in the image. Alternatively, it may be obtained from a contact sensor mounted at the subject.

Generally, a PPG signal results from variations of the blood volume in the skin. Hence the variations give a characteristic pulsatility "signature" when viewed in different spectral components of the reflected/transmitted light. This signature is basically resulting as the contrast (difference) of the absorption spectra of the blood and that of the blood-less skin tissue. If the detector, e.g. a camera or sensor, has a discrete number of color channels, each sensing a particular part of the light spectrum, then the relative pulsatilities in these channels can be arranged in a "signature vector", also referred to as the "normalized blood-volume vector", Pbv. It has been shown G. de Haan and A. van Leest, "Improved motion robustness of remote-PPG by using the blood volume pulse signature", Physiol. Meas. 351913, 2014, which is herein incorporated by reference, that if this signature vector is known then a motion-robust pulse signal extraction on the basis of the color channels and the signature vector is possible. For the quality of the pulse signal it is essential though that the signature is correct, as otherwise the known methods mixes noise into the output pulse signal in order to achieve the prescribed correlation of the pulse vector with the normalized color channels as indicated by the signature vector.

Details of the Pbv method and the use of the normalized blood volume vector (called "predetermined index element having a set orientation indicative of a reference physiological information") have also been described in US 2013/0271591 A1, which details are also herein incorporated by reference.

The computation unit may further be configured to compute said weights for weighting said at least two different wavelength channels. The same algorithms and methods as used for computing said reference signal may hereby be used. The weights may particularly be from a larger group of pixels and not from the local pixel values themselves (since the SNR is too low).

In still another embodiment said image generation unit is configured to further generate a motion map by computing a weighted difference between the generated amplitude map and a single-channel amplitude map generated from the image data of a single wavelength channel. Alternatively, this motion map may be computed as a weighted sum of the different wavelength channels directly, using the "signature"-vector of motion ([1 1 1] for a three wavelength system), i.e. using the knowledge that the relative strength of the motion signal is identical in all wavelength channels. The motion map may provide additional information useful for a diagnosis.

Furthermore, in an embodiment said image generation unit is configured to use one or more of said amplitude map, phase map and motion map to group image areas of the obtained image data showing motion artifacts below a predetermined motion artifact threshold or the smallest motion artifact and/or showing a ballistocardiographic motion above a predetermined ballistocardiographic motion threshold or the largest ballistocardiographic motion and/or showing a photoplethysmographic information above a predetermined photoplethysmographic information threshold or the strongest photoplethysmographic information. The grouping may also be iterated in order to select the best camera sensors (i.e. image areas in the obtained image frames) to provide the reference signal.

The image data are acquired by an imaging unit, in particular a camera, which acquires a temporal sequence of image frames of a skin region of the subject in at least two different wavelength channels. The imaging unit detects light, particularly in the wavelength interval between 400 nm and 1200 nm, transmitted through or reflected from the skin region, wherein said image data comprise wavelength-dependent reflection or transmission information in said at least two different wavelength channels.

Advantageously, said imaging unit comprises an optical sensing array, in particular a two-dimensional image sensor, including a Bayer-pattern filter providing at least three wavelength channels, in particular centered at approximately 450 nm, 550 nm and 650 nm or centered at approximately 650 nm, 750 nm and 850 nm (which may have the advantage that the penetration depth of the wavelengths is more comparable). However, it is also possible to use a separate 2D optical sensor for each individual wavelength (each 2D optical sensor being equipped with a different filter, e.g. for 650 nm, 750 nm and 850 nm). In this case the sensors should be aligned (to sense the same skin area). This may be done using optical means (e.g. a color-splitting prism), or using electronical means (e.g. image registration).

Generally, there exists a lot of freedom in choosing the wavelengths. It is advantageous if the wavelengths correspond to spectral regions where the blood absorption is very different, although there may be reasons that prevent the most logical choice here, like preference for invisible light, limitations of the sensor, availability of efficient light sources, etc.

Generally, the interaction of electromagnetic radiation, in particular light, with biological tissue is complex and includes the (optical) processes of (multiple) scattering, backscattering, absorption, transmission and (diffuse) reflection. The term "reflect" as used in the context of the present invention is not to be construed as limited to specular reflection but comprises the afore-mentioned types of interaction of electromagnetic radiation, in particular light, with tissue and any combinations thereof.

For obtaining a vital sign information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

The system may further comprise an illumination unit, such as a light source positioned remotely from the tissue, for illuminating the skin region of the subject with light in said at least two different wavelength channels. This further improves the acquisition of the image data and the quality of the obtained PPG image.

Preferably, said illumination unit is configured to emit modulated light having a modulation frequency outside the frequency band of the subject's pulse, in particular above 200 BPM. For instance, in an embodiment said illumination unit is configured to emit amplitude modulated light using a modulation signal, in particular $1+\beta \cdot \sin(1/2\pi f)$ with a small modulation factor $\beta$ in the range of $0.001<\beta<0.1$. Instead of modulating the illumination unit it is equally possible to apply this modulation to all individual wavelength channels using constant illumination, which provides a comparable effect.

In another embodiment the illumination unit is configured to emit polarized light and the imaging unit comprises a polarizer. This reduces the sensitivity for specular reflections on the skin.

BRIEF DESCRIPTION OF THE DRAWINGS

These and other aspects of the invention will be apparent from and elucidated with reference to the embodiments described hereinafter. In the following drawings.

DETAILED DESCRIPTION OF THE INVENTION

Figure 1:
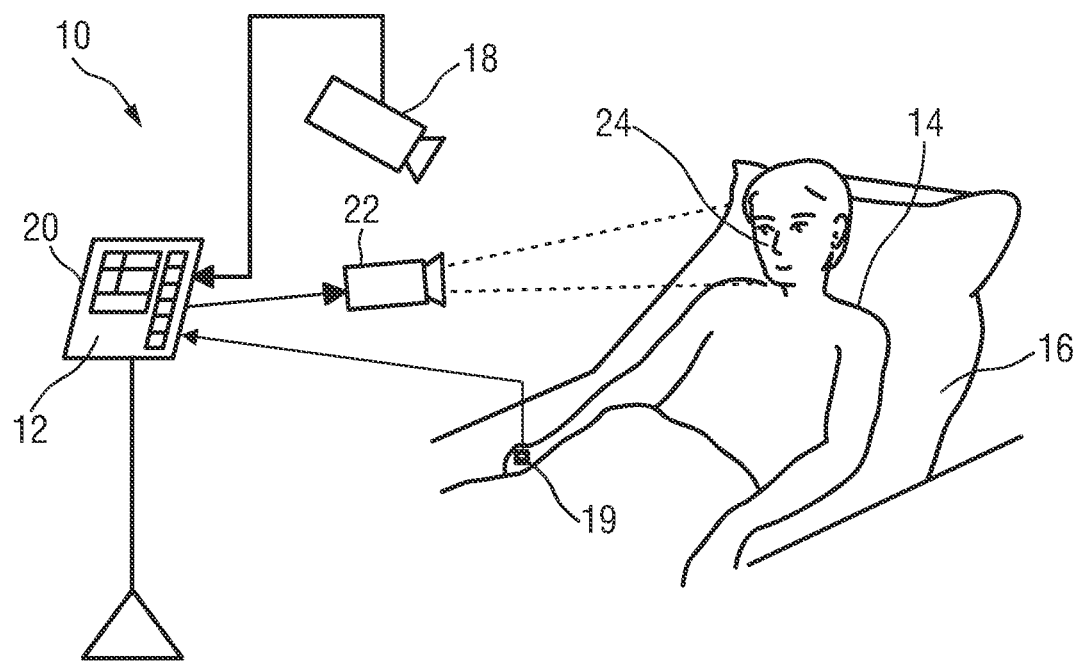
FIG. 1 shows a schematic diagram of a first embodiment of a system according to the present invention.

FIG. 1 shows a schematic diagram of a system 10 according to the present invention including a device 12 for generating a photoplethysmographic image (PPG image) carrying vital sign information (in particular a vital sign information signal) of a subject of a subject 14 from detected electromagnetic radiation transmitted through or reflected from a subject. The subject 14, in this example a patient, lies in a bed 16, e.g. in a hospital or other healthcare facility, but may also be a neonate or premature infant, e.g. lying in an incubator, or person at home or in a different environment, such as an athlete doing sports. The region of interest may be skin, but may also be an internal organ, in which case the images may be recorded in an operation theatre during surgery. In the following explanation a skin area will be used as an example for the region of interest, but the explanation shall be equally apply to an internal organ as region of interest.

For the following explanation, the vital sign information to be determined may be pulsatility or blood perfusion, but other kinds of vital sign information may also be obtained and depicted in a PPG image.

There exist different embodiments for an imaging unit (or detector) for detecting electromagnetic radiation transmitted through or reflected from a subject, which may alternatively (which is preferred) or together be used. In the embodiment of the system 10 two different embodiments of the imaging unit are shown and will be explained below. Both embodiments of the imaging are configured for acquiring image data of a skin region of a subject in at least two different wavelength channels, said image data comprising two or more image frames acquired by detecting light transmitted through or reflected from the skin region over time, wherein said image data comprise wavelength-dependent reflection or transmission information in said at least two different wavelength channels.

In one embodiment the imaging unit comprises a camera 18 (also referred to as camera-based or remote PPG sensor) including a suitable photosensor for (remotely and unobtrusively) capturing image frames of the subject 14, in particular for acquiring a sequence of image frames of the subject 14 over time, from which photoplethysmography signals can be derived. The image frames captured by the camera 18 may particularly correspond to a video sequence captured by means of an analog or digital photosensor, e.g. in a (digital) camera. Such a camera 18 usually includes a photosensor, such as a CMOS or CCD sensor, which may also operate in a specific spectral range (visible, IR) or provide information for different spectral ranges. The camera 18 may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color or a weighted sum of wavelengths). The image frames include at least some image pixels being representative of a skin portion of the subject. Thereby, an image pixel may correspond to one photosensitive element of a photo-detector and its (analog or digital) output or may be determined based on a combination (e.g. through binning, or spatial filtering) of a plurality of the photosensitive elements.

In another embodiment the imaging unit comprises one or more optical photoplethysmography sensor(s) 19 (also referred to as contact PPG sensor(s)) configured for being mounted to a skin portion of the subject 14 for acquiring photoplethysmography signals. The PPG sensor(s) 19 may e.g. be designed in the form of a patch attached to a subject's forehead for measuring the blood oxygen saturation or a heart rate sensor for measuring the heart rate, just to name a few of all the possible embodiments.

When using a camera 18 the system 10 may further optionally comprise an illumination unit 22 (also called illumination source or light source or electromagnetic radiator), such as a lamp or LED, for illuminating/irradiating a region of interest 24, such as the skin of the patient's face (e.g. part of the cheek or forehead), with light, for instance in a predetermined wavelength range or ranges (e.g. in the red, green and/or infrared wavelength range(s)). The light reflected from said region of interest 24 in response to said illumination is detected by the camera 18. In another embodiment no dedicated light source is provided, but ambient light is used for illumination of the subject 14. From the reflected light only light in a desired wavelength ranges (e.g. green and red or infrared light, or light in a sufficiently large wavelength range covering at least two wavelength channels) may be detected and/or evaluated.

The device 12 is further connected to an interface 20 for displaying the determined information and/or for providing medical personnel with an interface to change settings of the device 12, the camera 18, the PPG sensor(s) 19, the light source 22 and/or any other parameter of the system 10. Such an interface 20 may comprise different displays, buttons, touchscreens, keyboards or other human machine interface means.

A system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, a wearable, a handheld device like a smartphone, or the like. The uni- or bidirectional communication between the device 12, the camera 18, the PPG sensor(s) 19 and the interface 20 may work via a wireless or wired communication interface. Other embodiments of the present invention may include a device 12, which is not provided stand-alone, but integrated into the camera 18 or the interface 20.

There exist several known methods to obtain a pulse signal S from (normalized) detection signals $C_n$, said methods being referred to as ICA, PCA, Pbv, CHROM, and ICA/PCA guided by Pbv/CHROM, which have also been described in the above cited paper of de Haan and van Leest. These methods can be interpreted as providing the pulse signal S as a mixture of different wavelength channels, e.g. red, green and blue signals from a color video camera, but they differ in the way to determine the optimal weighting scheme. In these methods the resulting weights are aimed at a mixture in which the distortions disappear, i.e. the "weighting vector" is substantially orthogonal to the main distortions usually caused by subject motion and/or illumination variations.

In the following some basic considerations with respect to the Pbv method shall be briefly explained.

The beating of the heart causes pressure variations in the arteries as the heart pumps blood against the resistance of the vascular bed. Since the arteries are elastic, their diameter changes in sync with the pressure variations. These diameter changes occur even in the smaller vessels of the skin, where the blood volume variations cause a changing absorption of the light.

The unit length normalized blood volume pulse vector (also called signature vector) is defined as Pbv, providing the relative PPG-strength in the red, green and blue camera signal. To quantify the expectations, the responses $H_{red}(w)$, $H_{green}(w)$ and $H_{blue}(w)$ of the red, green and blue channel, respectively, were measured as a function of the wavelength w, of a global-shutter color CCD cameral, the skin reflectance of a subject, $\rho_s(w)$, and used an absolute PPG-amplitude curve PPG(w). From these curves, shown e.g. in FIG. 2 of the above cited paper of de Haan and van Leest, the blood volume pulse vector $P_{bv}$ is computed as:

$$\vec{P}_{bv}^T = \begin{bmatrix} \dfrac{\int_{w=400}^{700} H_{red}(w)I(w)PPG(w)dw}{\int_{w=400}^{700} H_{red}(w)I(w)\rho_a(w)dw} \\ \dfrac{\int_{w=400}^{700} H_{green}(w)I(w)PPG(w)dw}{\int_{w=400}^{700} H_{green}(w)I(w)\rho_a(w)dw} \\ \dfrac{\int_{w=400}^{700} H_{blue}(w)I(w)PPG(w)dw}{\int_{w=400}^{700} H_{blue}(w)I(w)\rho_a(w)dw} \end{bmatrix}$$

which, using a white, halogen illumination spectrum I(w), leads to a normalized Pbv=[0.27, 0.80, 0.54]. When using a more noisy curve the result may be Pbv=[0.29, 0.81, 0.50].

The blood volume pulse predicted by the used model corresponds reasonably well to an experimentally measured normalized blood volume pulse vector, Pbv=[0.33, 0.77, 0.53] found after averaging measurements on a number of subjects under white illumination conditions. Given this result, it was concluded that the observed PPG-amplitude, particularly in the red, and to a smaller extent in the blue camera channel, can be largely explained by the crosstalk from wavelengths in the interval between 500 and 600 nm. The precise blood volume pulse vector depends on the color filters of the camera, the spectrum of the light and the skin-reflectance, as the model shows. In practice the vector turns out to be remarkably stable though given a set of wavelength channels (the vector will be different in the infrared compared to RGB-based vector).

It has further been found that the relative reflectance of the skin, in the red, green and blue channel under white illumination does not depend much on the skin-type. This is likely because the absorption spectra of the blood-free skin is dominated by the melanin absorption. Although a higher melanin concentration can increase the absolute absorption considerably, the relative absorption in the different wavelengths remains the same. This implies an increase of melanin darkens the skin, but hardly changes the normalized color of the skin. Consequently, also the normalized blood volume pulse $P_{bv}$ is quite stable under white illumination. In the infrared wavelengths the influence of melanin is further reduced as its maximum absorption occurs for short wavelengths (UV-light) and decreases for longer wavelengths.

The stable character of Pbv can be used to distinguish color variations caused by blood volume change from variations due to alternative causes. The resulting pulse signal S using known methods can be written as a linear combination (representing one of several possible ways of "mixing") of the individual DC-free normalized color channels:

$$S = W C_n$$

with $WW^T=1$ and where each of the three rows of the 3×N matrix $C_n$ contains N samples of the DC-free normalized red, green and blue channel signals $R_n$, $G_n$ and $B_n$, respectively, i.e.:

$$\vec{R}_n = \frac{1}{\mu(\vec{R})}\vec{R} - 1, \vec{G}_n = \frac{1}{\mu(\vec{G})}\vec{G} - 1, \vec{B}_n = \frac{1}{\mu(\vec{B})}\vec{B} - 1.$$

Here the operator μ corresponds to the mean. Key difference between the different methods is in the calculation of the weighting vector W. In one method, the noise and the PPG signal may be separated into two independent signals built as a linear combination of two color channels. One combination approximated a clean PPG signal, the other contained noise due to motion. As an optimization criterion the energy in the pulse signal may be minimized. In another method a linear combination of the three color channels may be used to obtain the pulse signal. In still further methods, the ICA or the PCA may be used to find this linear combination. Since it is a priori unknown which weighted color signal is the pulse signal all of them used the periodic nature of the pulse signal as the selection criterion.

The Pbv method generally obtains the mixing coefficients using the blood volume pulse vector as basically described in US 2013/271591 A1 and the above cited paper of de Haan and van Leest. The best results are obtained if the band-passed filtered versions of $R_n$, $G_n$ and $B_n$ are used. According to this method the known direction of Pbv is used to discriminate between the pulse signal and distortions. This not only removes the assumption (of earlier methods) that the pulse is the only periodic component in the video, but also eliminates assumptions on the orientation of the distortion signals. To this end, it is assumed as before that the pulse signal is built as a linear combination of normalized color signals. Since it is known that the relative amplitude of the pulse signal in the red, green and blue channel is given by Pbv, the weights, $W_{PBV}$, are searched that give a pulse signal S, for which the correlation with the color channels $R_n$, $G_n$, and $B_n$ equals Pbv $$\vec{S}C_n^T = k\vec{P}_{bv} \Leftrightarrow \vec{W}_{PBV}C_n C_n^T = k\vec{P}_{bv}, \quad (1)$$

and consequently the weights determining the mixing are determined by $$\vec{W}_{PBV} = k\vec{P}_{bv}Q^{-1} \text{ with } Q = C_n C_n^T, \quad (2)$$

and the scalar k is determined such that $W_{PBV}$ has unit length. It is concluded that the characteristic wavelength dependency of the PPG signal, as reflected in the normalized blood volume pulse, Pbv, can be used to estimate the pulse signal from the time-sequential RGB pixel data averaged over the skin area. This algorithm is referred to as the $P_{bv}$ method.

Hence, as explained above, a pulse signal results as a weighted sum of the at least two detection signals $C_n$. Since all detection signals $C_n$ contain the pulse and different levels of (common) noise, the weighting (of the detection signals to obtain the pulse signal) can lead to a pure noise-free pulse. This is why ICA and PCA can be used to separate noise and pulse. According to the present invention this is done differently.

Figure 2:
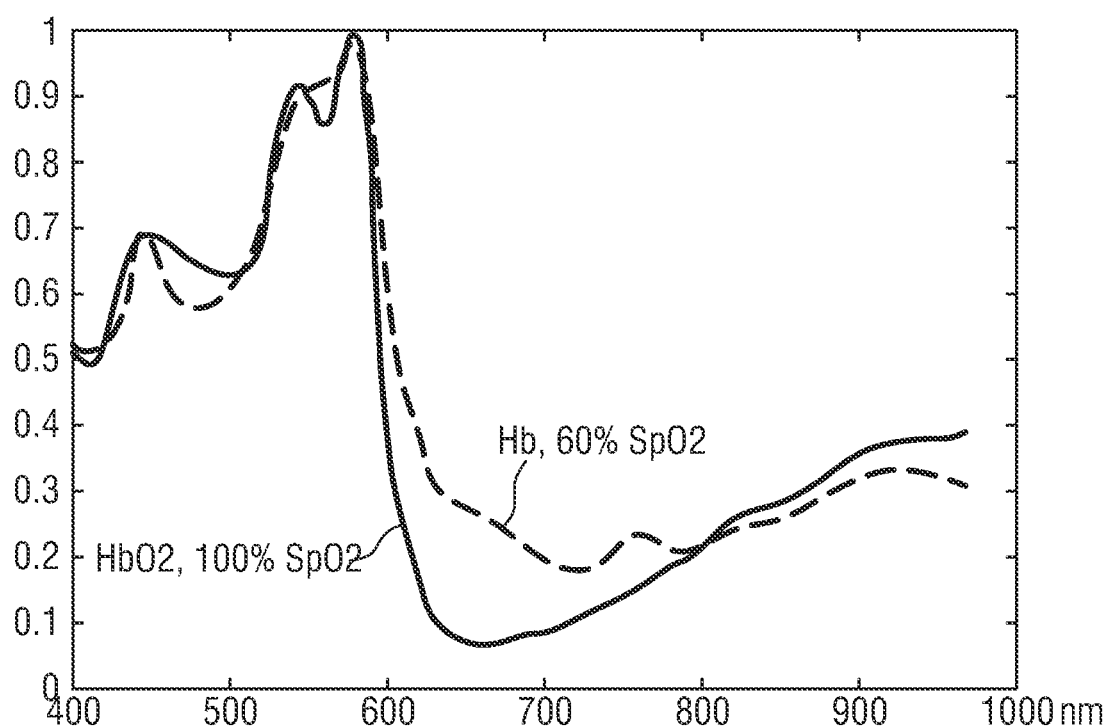
FIG. 2 shows a diagram of the absorption spectrum of oxygenated and non-oxygenated blood.

FIG. 2 shows a diagram of the absorption spectra of blood for oxygenated blood (SpO2=100%) and non-oxygenated blood (SpO2=60%). As can be seen, the absorption spectrum of blood depends on the oxygen saturation, particularly in the wavelengths around 650 nm. It is clear from FIG. 2 though that the absorption in the green wavelength range (around 550 nm) and blue wavelength range (around 450 nm) is much higher.

Figure 3:
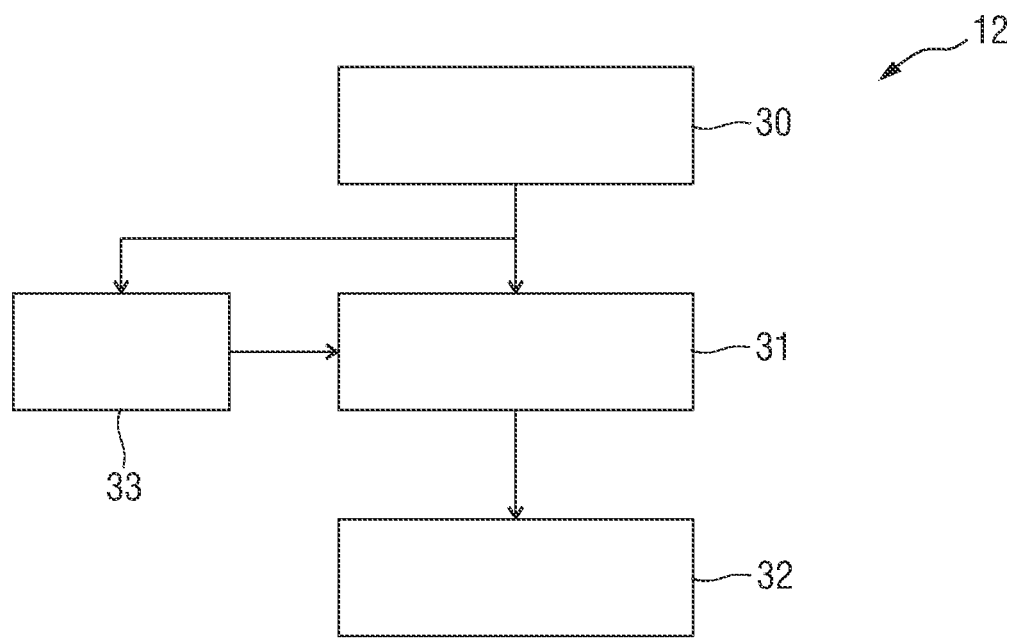
FIG. 3 shows a schematic diagram of a first embodiment of a device according to the present invention.

FIG. 3 shows a schematic illustration of an embodiment of the device 12 according to the present invention. The device 12 comprises an input interface 30 for obtaining image data of a skin region of a subject in at least two different wavelength channels, said image data comprising two or more image frames acquired by detecting light transmitted through or reflected from the skin region over time, wherein said image data comprise wavelength-dependent reflection or transmission information in said at least two different wavelength channels. A combination unit 31 combines, per pixel or group of pixels and per time instant, image data values of said at least two different wavelength channels to obtain a time-variant pulse signal per pixel or group of pixels. An image generation unit 32 generates a photoplethysmographic image from a property of the respective pulse signals in a time window including at least two image frames. The device 12 may e.g. be implemented in the form of a processor or computer, i.e. in software and/or hardware.

Preferably, the combination unit 31 combines the image data from the different wavelength channels as a weighted average of temporally normalized channels in a temporal window, such that the sum of the weights is substantially zero, and image generation unit 32 computes an amplitude- and/or phase-map of the time-variations for each (group of) pixels as the output image, i.e. of the temporal variations of said time-variant pulse signals as photoplethysmographic image. Hereby, the amplitude map may be computed as inner product of the respective pulse signal with a reference signal and/the phase of the phase map may be computed with respect to a reference signal, which may be obtained by averaging all, or a subset of, the signals and normalizing the result). Similarly, the phase of the phase map may be computed with respect to a reference signal, which may be obtained from a contact sensor or from a signal obtained by averaging the signals of a selected group of pixels in the image.

The device 12 thus is not merely applying known motion robust PPG extraction, as described in many publications, per group of pixels. This would not work out well, since the thus-obtained channel weights would be too noisy, which would lead to inaccurate PPG amplitudes. The reasons are the limited number of pixels that are averaged per sensor, and the very small motion distortions in the typically immobilized body part. To solve this issue, multiplicative noise or a modulated light source may be applied in preferred embodiments (both are options to emulate stronger motion) to obtain stable weights suitable to suppress motion (using e.g. known motion robust PPG extraction methods on a relatively large skin area). These resulting weights are then successively used on individual pixel (groups) for channel mapping.

In an embodiment said image generation unit 32 is configured to determine, per pulse signal, a function of one or more of the pulsatility, amplitude, phase and standard deviation in said time window and to use the determined function of pulsatility, amplitude, phase and/or standard deviation as image data value of the PPG image at the spatial location corresponding to the respective pulse signal. Hence, for each image pixel (spation location) of the PPG image a corresponding pulse signal for said location is analyzed within a time window, in particular a selected property is analyzed, which may be pulsatility, amplitude, phase and/ standard deviation. The result of this analysis or a function of the analyzed property, e.g. the pulsatility itself or an average of the amplitude, is then used as the pixel value at this particular pixel of the PPG image.

Optionally, the device 12 further comprises a computation unit 33 for computing weights for determining the above mentioned weighted averages and/or for computing said above mentioned reference signal using a motion-robust photoplethysmography signal extraction algorithm. The weights and/or said reference signal may hereby be computed from a larger skin area covered by a plurality of pixels in said image frames using one or the above mentioned normalized blood volume pulse vector signature based method (Pbv method), a chrominance based method (CHROM), a blind source separation (BSS) method, a principal component analysis (PCA) or an independent component analysis (ICA).

In more detail, a reference signal may be obtained from a region of interest (ROI) within the recorded image frames, with a high ratio between signal and noise-plus interference (e.g., minimizing sensor noise by selecting a large ROI, reducing motions physically by immobilization, uniform lighting conditions during data acquisition, etc.). The pixels of this reference ROI are combined (e.g. averaged), the result being a modulated stream per each camera channel. These streams are then preferably fed to the CHROM or Pbv method. Both these methods produce weights given to the individual wavelength channels to obtain a motion robust output PPG signal. The resulting weights of either method can consequently be used for the channel-mapping of all pixels or groups of pixels.

As output image a motion map may be determined, which results as a weighted difference between the amplitude map resulting from channel mapping and an amplitude map from a single wavelength channel. Alternatively, a weighted sum of the different wavelength channels, reflecting the motion map, may be computed directly.

Further, one or more of said amplitude map, phase map and motion map may be used to group image areas of the obtained image data showing motion artifacts below a predetermined motion artifact threshold or the smallest motion artifact and/or showing a ballistocardiographic motion above a predetermined ballistocardiographic motion threshold or the largest ballistocardiographic motion and/or showing a photoplethysmographic information above a predetermined photoplethysmographic information threshold or the strongest photoplethysmographic information. Hence, camera sensors may be grouped (e.g. into a group with low-level motion artifacts, or a group with high level of BCG-motion, etc.). The signals from the grouped sensors may be combined into single signals for further analysis (e.g. waveform of PPG/BCG-signals). The grouping may also be iterated in order to select the best camera-sensors to provide a high quality reference signal, prior to deriving the physiological information. Examples of skin sites where BCG-motion is expected to be strong are e.g., carotid artery at the neck, brachial artery at the wrist, femoral artery and popliteal artery at the lower limbs, etc. Further examples are high-contrast areas (e.g. wrinkles, hairs) and edges (boundaries of an image part, e.g. space between two fingers), and body parts that are hard to immobilize, like eyes.

Still further, a series of output images obtained from time-shifted time windows is computed and shown sequentially. The time windows of successive output images may or may not be partially overlapping.

Figure 4:
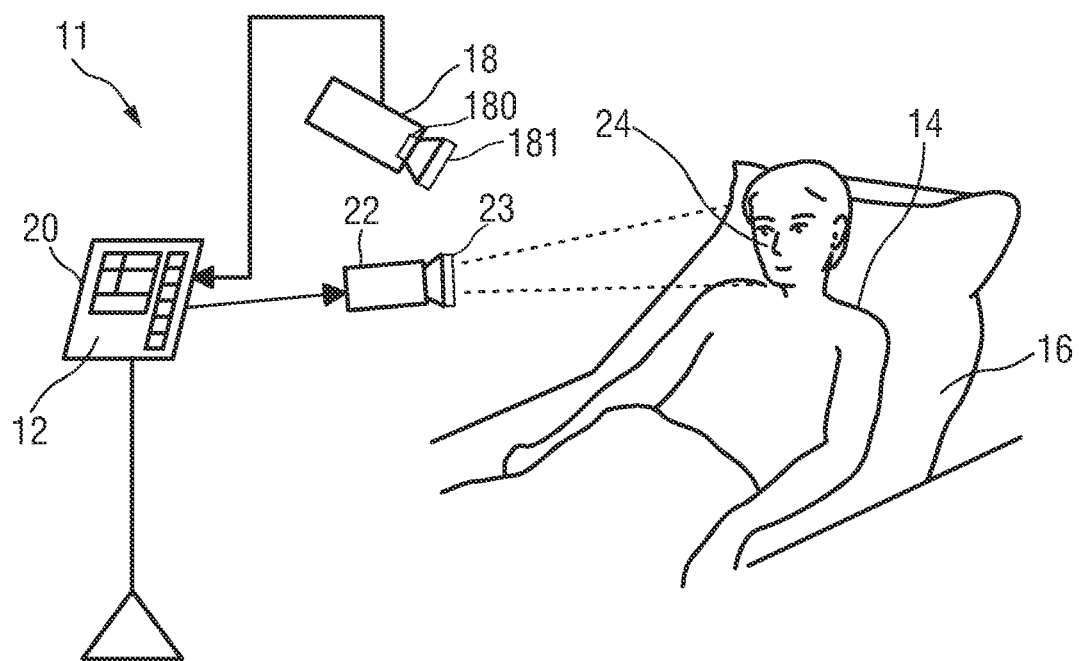
FIG. 4 shows a schematic diagram of a second embodiment of a system according to the present invention.

FIG. 4 shows a schematic diagram of a second embodiment of a system 11 according to the present invention. In this embodiment the camera 18 comprises an optical sensing array, in particular a two-dimensional image sensor, including a Bayer-pattern filter 180 providing at least three wavelength channels, in particular centered at approximately 450 nm, 550 nm and 650 nm or centered at approximately 650 nm, 750 nm and 850 nm. In another embodiment (not shown) separate two-dimensional image sensors may be used, one for each respective wavelength channel.

The illumination unit 22 preferably emits light in a wavelength range covering the three wavelength channels, i.e. in a range between 400 nm and 1200 nm. The illumination unit may even be configured to emit light at the same wavelength channels as mentioned above, i.e. centered at approximately 450 nm, 550 nm and 650 nm or centered at approximately 650 nm, 750 nm and 850 nm.

The illumination unit 22 may further be configured or controlled to emit modulated light having a modulation frequency outside the frequency band of the subject's pulse, in particular above 200 BPM. Particularly, amplitude modulated light may be emitted using a modulation signal, in particular $1+\beta \cdot \sin(1/2\pi(f)$ with a small modulation factor $\beta$ in the range of $0.001 < \beta < 0.1$.

Still further, the illumination unit may emit polarized light using a polarizer 23, and the imaging unit 18 may also comprise a corresponding polarizer 181 to reduce the sensitivity for specular reflections on the skin. To this end, the polarizers 23 and 181 may be orthogonal, such that primarily the scattered light that returns after penetrating the skin reaches the camera, while the specularly reflected light, which has the same polarization as the light-source, is substantially blocked.

Figure 5:
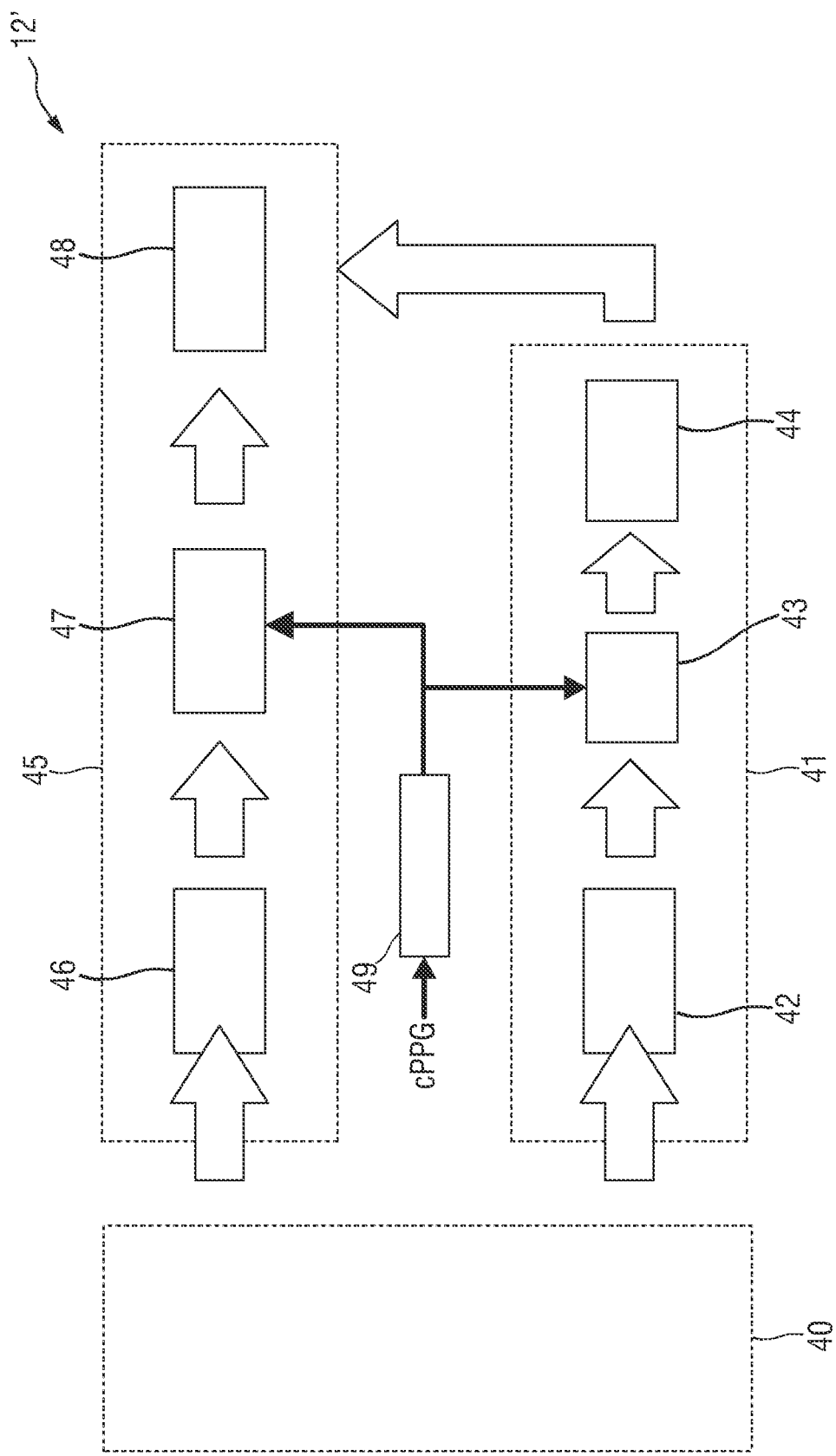
FIG. 5 shows a schematic diagram of a second embodiment of a device according to the present invention.

FIG. 5 shows a schematic diagram of a second embodiment of a device 12' according to the present invention. In a preprocessing unit 40 image frames are registered with respect to a central image frame of an acquired video sequence. A Horn-Schunck algorithm may be used to ensure stabilization against small movements, even at wrinkles and contours of the skin. The resulting image frames are subsequently denoised by Gaussian blurring and reduced by a factor of 5. Each pixel in the obtained images are referred to as a sensor element. Finally, skin sensors are segmented from background (dark, textureless) by color thresholding, and a large reference skin ROI (ROI Skin) is (preferably manually) demarcated, e.g. at the palm.

To obtain a reference remote PPG (rPPG) signal in a reference signal generation unit 41, a raw RGB stream is extracted from a user-defined ROI, e.g. at the palm. In a mapping unit 42 the reference signal is first low pass filtered to extract its "DC" component (e.g. using a 9th order Butterworth filter; cutoff frequency, 20 BPM) and normalized as AC/DC. The signals are then processed in strides of 128 samples (corresponding to about 10 cardiac cycles) with an overlapping factor of 50%. Each stride is detrended, multiplied with a Hanning window and filtered in the frequency domain by selection of heart rate component(s). The heart rate measurements (i.e. the instantaneous pulse rate) is obtained from pulse oximetry (cPPG), e.g. through peak detection in a detection unit 49. The heart rate measurements obtained by contact PPG (cPPG) are used to select either one or more harmonics of the pulse signal. This is referred to as adaptive bandpass filtering (ABPF) in ABPF unit 43. The signal is then, in transformation unit 44, Hilbert-transformed and normalized to unit norm as $\Sigma Re[\tilde{x}_{ref}]\tilde{x}_{ref}=1$.

The initial processing stages in a local signal generation unit 45 for obtaining a local rPPG amplitude and phase in each sensor element are similar to those of the reference remote PPG signal in unit 41, i.e., the raw RGB streams in each column m and linen of the sensor array are, in a mapping unit 46, normalized to AC/DC, mapped according to CHROM or PBV and, in an ABPF unit 47, adaptively bandpass filtered. The value of the PPG image at (m, n), obtained in a correlation unit 48, is the normalized inner-product between $X_{skin}$ and $S_{m,n}$, i.e.

$PPGI_{m,n}=\sqrt{2/L}\Sigma_{l=1}^{L}S_{m,n}(l)\tilde{x}_{Ref}(l)$.

In the described embodiments, so far, the "PBV-method" as described e.g. in the above cited paper of G. de Haan and A. van Leest, "Improved motion robustness of remote-PPG by using the blood volume pulse signature", is used as a basis for the computations. In further embodiments it is possible to use alternatives to $W_{PBV}$. It is equally possible to use any of the other methods mentioned in this paper to compute the weights used to combine the color channels to a vital sign signal with minimal distortions. Particularly, a good solution also results when using the chrominance based method, "CHRO", but also the "guided BSS-based methods" and even the older BSS-based methods, using periodicity of the pulse signal for component selection, provide viable options. Generally, the weights are calculated from the color signals filtered to include at least the pulse signal variations, in case only two wavelength channels are used, e.g. green and red, the difference of the normalized green and red also provides a viable option, which can mathematically be shown to approximate the ratio of green and red channels (motion has same strength in both channels and falls out, Pulsatility is different and remains. In this case fixed weights (1 and −1:Gn−Rn=Gn/Rn) may be used).

The present invention considers, for the first time, cancellation of ballistocardiographic artifacts in remote PPG images by means of signal processing. As this kind of motion is synchronous with the cardiac signal, common strategies to enhance the motion robustness are ineffective against this interfering source, and risks are that artifacts are confounded with actual PPG signals. According to the present invention, a step further has been taken to improving validity of PPG images by demonstrating that two known motion-robust channel mapping algorithms previously reported for heart rate detection in the remote-PPG literature, namely CHROM and PBV, can be extended to PPG imaging. These offer the advantage of eliminating motion sources in remote PPG sensor elements, irrespective of whether they are cardiac-related or from other sources, with the added benefit of compensating artifacts resulting from non-orthogonal illumination in curved skin surfaces. Performance gains resulting from motion robust channel-mapping are cumulative with additional practices or signal processing approaches aiming at improved PPG-image formation.

The joint representation of the normalized Fourier coefficients for remote-PPG signals (a surrogate of blood-volume changes at the capillary bed) and BCG-artifacts (a surrogate of arterial motion) further confirms that these signals are slightly different and must not be confused. Using the same recordings, the feasibility of BCG-artifact cancellation by mapping normalized data from the PPG sensor elements prior to PPG image formation has been confirmed. Using the CHROM- or PBV-based imaging frameworks, it was observed that the PPG amplitude in the palm region is stronger than at the wrist, for all subjects. In the corrected phase images, differences in the order of 20-30 degrees were observed between the center of the palm and wrist, and the periphery of the palm; these are largely independent of illumination conditions, i.e., lateral or homogeneous illumination show similar results. Pulse-induced skin motion patterns are most prominent under non-uniform lighting conditions, though, to a minor extent, BCG-artifacts also occur under uniform lighting conditions, at high spatial frequency sites, as are edges, wrinkles, and even the texture of the skin.

In this investigation, both algorithms performed comparably. In practical scenarios, the preference from one method over the other should depend upon the relative ease of estimating the blood-volume pulse vector, PBV or the trust in the assumed "standard skin-tone vector". Performance benefits resulting from the inclusion of two additional harmonics of the pulse-rate frequency were assessed, and it was found that it resulted in just marginal improvements in detail and NRMS performance of the resulting PPG images.

The above described embodiments have mainly been explained with respect to contactless sensors. Generally, the same methods can also be used for contact sensors. By way of example, the present invention can be applied in the field of health care, e.g. unobtrusive remote patient monitoring, general surveillances, security monitoring and so-called lifestyle environments, such as fitness equipment, or the like. Applications may include a finger oximeter or unobtrusive monitoring. Particularly for new diagnostic means, e.g. for wound-healing, analysis of lesions (on-skin or internally after or during surgery), and cancer-detection (on skin, e.g. melanoma, but maybe also in-body, e.g. oesophagus-cancer, colon-cancer, etc.).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for generating a photoplethysmographic image carrying vital sign information of a subject, said device comprising:
    an input interface unit that obtains image data of a skin region of a subject in at least two different wavelength channels, wherein said image data comprises two or more image frames acquired by detecting light transmitted through or reflected from the skin region over time, and wherein said image data comprise wavelength-dependent reflection or transmission information in said at least two different wavelength channels;

a combination unit that combines, per pixel or group of pixels and per time instant, image data values of said at least two different wavelength channels to obtain a time-variant pulse signal per pixel or group of pixels, wherein the combination unit is configured to combine the image data values of said at least two different wavelength channels are combined as a weighted combination of one of temporally normalized wavelength channels or of the logarithm of wavelength channels, and wherein the sum of the weights used for the combination is zero;

an image generating unit that generates a photoplethysmographic image from a property of the respective pulse signals in a time window including at least two image frames, wherein the image generation unit is configured to compute at least one of an amplitude map and a phase map of the temporal variations of the time-variant pulse signals as the photoplethysmographic image, and wherein the image generation unit is configured to compute at least one of:

the amplitude map as an inner product of the respective pulse signal with a reference signal, and the phase of the phase map with respect to a reference signal; and a computation unit that computes weights for determining said weighted averages and/or that computes said reference signal from a skin area covered by a plurality of pixels in said image frames.

2. The device as claimed in claim 1, wherein said computation unit being configured to compute said weights and/or said reference signal from a skin area covered by the plurality of pixels in said image frames is based on a normalized blood volume pulse vector signature based method, a chrominance based method, a blind source separation method, a principal component analysis or an independent component analysis.

3. The device as claimed in claim 1, wherein said image generation unit is configured to further generate a motion map by computing weighted difference between the generated amplitude map and a single-channel amplitude map generated from the image data of a single wavelength channel or by computing a weighted sum of the different wavelength channels.

4. The device as claimed in claim 1, wherein said image generation unit is configured to process one or more of said amplitude map, phase map and motion map to group image areas of the obtained image data showing motion artifacts below a predetermined motion artifact threshold or the smallest motion artifact and/or showing a ballistocardiographic motion above a predetermined ballistocardiographic motion threshold or the largest ballistocardiographic motion and/or showing a photoplethysmographic information above a predetermined photoplethysmographic information threshold or the strongest photoplethysmographic information.

5. A system for generating a photoplethysmographic image carrying vital sign information of a subject, said system comprising:

an imaging unit for acquiring image data of a skin region of a subject in at least two different wavelength channels, said image data comprising two or more image frames acquired by detecting light transmitted through or reflected from the skin region over time, wherein said image data comprise wavelength-dependent reflection or transmission information in said at least two different wavelength channels;

an input interface unit that obtains image data of a skin region of a subject in at least two different wavelength channels, wherein said image data comprises two or more image frames acquired by detecting light transmitted through or reflected from the skin region over time, and wherein said image data comprise wavelength-dependent reflection or transmission information in said at least two different wavelength channels;

a combination unit that combines, per pixel or group of pixels and per time instant, image data values of said at least two different wavelength channels to obtain a time-variant pulse signal per pixel or group of pixels, wherein the combination unit is configured to combine the image data values of said at least two different wavelength channels are combined as a weighted combination of one of temporally normalized wavelength channels or of the logarithm of wavelength channels, and wherein the sum of the weights used for the combination is substantially-zero;

an image generating unit that generates a photoplethysmographic image from a property of the respective pulse signals in a time window including at least two image frames, wherein the image generation unit is configured to compute at least one of an amplitude map and a phase map of the temporal variations of the time-variant pulse signals as the photoplethysmographic image, and wherein the image generation unit is configured to compute at least one of:

the amplitude map as an inner product of the respective pulse signal with a reference signal, and the phase of the phase map with respect to a reference signal; and a computation unit that computes weights for determining said weighted averages and/or that computes said reference signal from a skin area covered by a plurality of pixels in said image frames.

6. The system as claimed in claim 5, wherein said imaging unit comprises an optical sensing array including a Bayer-pattern filter providing at least three wavelength channels centered at 450 nm, 550 nm and 650 nm or centered at 650 nm, 750 nm and 850 nm.

7. The system as claimed in claim 5, further comprising an illumination unit for illuminating the skin region of the subject with light in said at least two different wavelength channels.

8. The system as claimed in claim 5, wherein said illumination unit is configured to emit modulated light having a modulation frequency outside the frequency band of the subject's pulse.

9. The system as claimed in claim 8, wherein said illumination unit is configured to emit amplitude modulated light based on a modulation signal.

* * * * *